United States Patent [19]

Bowen

[11] Patent Number: 5,792,821
[45] Date of Patent: Aug. 11, 1998

[54] POLYMERIZABLE CYCLODEXTRIN DERIVATIVES

[75] Inventor: Rafael L. Bowen, Gaithersburg, Md.

[73] Assignee: American Dental Association Health Foundation, Gaithersburg, Md.

[21] Appl. No.: 779,276

[22] Filed: Jan. 6, 1997

[51] Int. Cl.$^6$ ............................................... C08F 224/00
[52] U.S. Cl. .................................................. 526/238.2
[58] Field of Search ............................... 526/238.2

[56] References Cited

U.S. PATENT DOCUMENTS

| | | | |
|---|---|---|---|
| 3,565,887 | 2/1971 | Parmerter et al. | 526/238.2 |
| 4,906,488 | 3/1990 | Pera . | |
| 5,258,414 | 11/1993 | Bergishagen . | |
| 5,268,286 | 12/1993 | Kobayashi et al. . | |
| 5,290,831 | 3/1994 | Di Ruocco . | |
| 5,357,012 | 10/1994 | Nusstein et al. . | |
| 5,362,496 | 11/1994 | Baker et al. . | |
| 5,414,075 | 5/1995 | Swan et al. . | |
| 5,416,181 | 5/1995 | Nguyet et al. . | |

OTHER PUBLICATIONS

Fietzek PP, Kuhn K (1976). The primary structure of collagen. In: International review of connective tissue research, vol. 7. Hall DA, Jackson DS, editors. New York: Academic Press, pp. 28–29.

Takeo K. Hirose K. Kuge T (1973). Carbon–13 nuclear magnetic resonance spectra of cyclodextrins and its peracetates. *Chemistry Letters*, published by the Chemical Society of Japan, pp. 1233–1236.

Bender ML, Komiyama M (1978). Cyclodextrin chemistry. New York: Springer–Verlag, pp. 1–39.

Bowen RL (1961). Investigation of the Surfaces of Hard Tooth Tissues by a Surface Activity Test. In: Proceedings of the Workshop on Adhesive Restorative Dental Materials. Phillips R, Ryge G, editors. At Indiana University, Sep. 28–29, Spencer, Indiana; Owen Litho Service, pp. 177–191.

Bowen RL (1996) Synthesis of Beta Cyclodextrin Methacrylates for Potential Uses in Dental Resins. J. Dent. Res., vol. 75:347, Abstract No. 2640.

Breslow R (1984). Enzyme models related to inclusion compounds. In: Inclusion compounds, vol. 3. Atwood JL, Davies JED, MacNicol DD, editors New York: Academic Press, pp. 484–508.

Casu B, Reggiani M, Gallo GG, Vigevani A (1968). Conformation of O–methylated amylose and cyclodextrins. Tetrahedron, 24:803–821.

Colson P, Jennings HJ, Smith Ian–CP (1974). Composition, sequence, and conformation of polymers and oligomers of glucose as revealed by carbon–13 nuclear magnetic resonance. JACS 96:8083–8086.

Harata K (1991). Recent advances in the X–ray analysis of cyclodextrin complexes. In: Inclusion compounds, vol. 5. Atwood JL, Davies JED, MacNicol DD, editors. New York: Oxford University Press, p. 342.

Poudrier JK (1995). Corn meets nanotechnology and they're getting along "amazingly" well. Today's Chemist at Work, Feb., pp. 25–30, 1996.

Saenger W (1984). Structural aspects of cyclodextrins and their inclusion complexes. In: Inclusion compounds, vol. 2 Atwood JL, Davies JED, MacNicol DD, editors. New York: Academic Press, pp. 231–259.

Szejtli (1984). Industrial applications of cyclodextrins. In: Inclusion compounds, vol. 3. Atwood JL, Davies JED, MacNicol DD, editors. New York: Academic Press, pp. 331–351.

Technical Bulletin (1966). Dimethyl sulfoxide. Crown Zellerbach Corporation, Chemical Products Division, Camas, Washington 98607, p. 10.

*Primary Examiner*—Joseph L. Schofer
*Assistant Examiner*—Wu C. Cheng
*Attorney, Agent, or Firm*—Banner & Witcoff Ltd

[57] ABSTRACT

Polymerizable cyclodextrin derivatives (PCDs) are disclosed, wherein each molecule contains at least one covalently attached polymerizable group, may also contain one or more other covalently attached functional ligand group(s), such as free carboxyl group(s), may also contain molecularly encapsulated comonomers, polymerization inhibitors (stabilizers), and polymerization initiators. The groups are attached covalently as ether or ester derivatives in statistically predetermined proportions, in a homogeneous solution, to form a "combinatorial" library having quasi-random molecular configurations of free carboxyl or other ligand groups. In the resulting PCD library, appropriate comonomers and polymerization initiators can be added that will enable timely polymerization to form unique structural adhesives and resins. The adhesive resins can be utilized in preventative and restorative dentistry.

2 Claims, No Drawings

5,792,821

1

POLYMERIZABLE CYCLODEXTRIN DERIVATIVES

This invention was made in the course of research partially supported by a grant from the National Institute of Dental Research (Grant Number DE05129-20). The U.S. Government has certain rights in the invention.

BACKGROUND OF THE INVENTION

1. Field of the Invention

This invention generally relates to polymerizable monomers that have a multiplicity of functional groups, which compositions are useful as components of dental and industrial formulations for a number of specific applications. The principle focus is on functionalized methacrylated cyclodextrins, preferably beta-cyclodextrins because of availability and economic considerations. However, alpha- and gamma-cyclodextrins and the hydroxyalkylated derivatives of all three fall within the scope of this invention, as do mixtures of these various kinds of cyclodextrins and their derivatives (CDS), preferably with the stoichiometric equivalence of hydroxyl groups being taken into account in the preparation of the inventive polymerizable cyclodextrin derivatives ("PCDs").

Although there are reported to be over 10,000 citations regarding cyclodextrins and their derivatives in the literature, it was surprising to discover in an extensive search that there was apparently no discovery or teaching of an art relating to the production and use of cyclodextrin derivatives in dental materials such as described in the present invention. The present invention relates to preparation methods and utilizations in a spectrum of dental and other uses.

On one end of the spectrum are highly substituted or derivatized cyclodextrins containing many polymerizable groups, for example, methacrylate and/or acrylate ester moieties, plus or minus other organophilic groups to provide organophilic characteristics for use in dental sealant resins and dental and other composites. These are expected to yield formulations with less polymerization shrinkage in comparison to contemporary materials of equal viscosity. The basis for this is the quasi-spherical configuration of these high-volume crosslinking monomers together with the prediction of compactness, or high density, of monomeric formulations containing comonomers that can fit within the monomeric methacrylated cyclodextrin derivative (MCD) or polymerizable cyclodextrin derivative (PCD) molecules while liquid, but become "external" chain segments during polymerization.

Farther over in this spectrum lie compounds of intermediate hydrophilicity. These compounds comprise derivatives of combinatorial syntheses of cyclodextrins containing at least one and preferably more than one polymerizable group on each molecule together with, and also on each of the same molecules, one and preferably more than one ligand group (s) selected from those that can form hydrogen bonds, ionic bonding interactions, π interactions, hydrophobic bonds, and/or van der Waals interactions with corresponding substrate groups.

On the other hand, a minimal number, one or preferably two or more, of organophilic polymerizable groups, together with a large number of hydrophilic polar ligand groups can be obtained on molecules in the resulting assortment of compounds for applications such as penetration and adhesive bonding to appropriate hydrophilic substrates, the formation of dental and other cements, and other medical and industrial applications. For example, on this end of this

2 spectrum, these derivatives of cyclodextrin can have a large number of carboxyl ligand groups and a small number of polymerizable groups for formulations to be used in novel cements, including those resembling dental "glass-ionomer cements," zinc oxide-based cements, calcium ion-based cements, and cements comprising admixtures of di- and polyvalent cations with compounds falling within the scope of this invention.

The combinatorial syntheses of the present invention yield mixtures of (co)polymerizable cyclodextrin derivatives (PCDs). The derived mixture or "library," of combinations and permutations and the configurations of the molecules resulting from syntheses as described herein would, when properly formulated with other comonomers and auxiliary components well known to the art, and applied to dental surfaces, bind preferentially to substrate sites containing some threshold number and/or strength of interactions. As the assortment of molecules diffuses into the substrate layers, the particular molecules that find such "docking sites" will be held in that position while molecules of other configurations will continue to diffuse at random through the substrate surface layers until they find different surface sites to which they would be strongly bound. Eventually those not finding sites would constitute part of the monomers that would fill the remaining spaces between the intra-substrate, surface-bound monomers. With appropriate polymerization initiators, both would subsequently form a three-dimensional crosslinked polymeric network to provide improved bonding between the substrate material and overlying polymers.

One of the most problematic substrates for dental adhesive bonding is that of the dentin portion of teeth needing repair. Current techniques involve light acid etching to remove material that is weakly attached to the dentin or enamel surfaces. This acid treatment also dissolves some of the surface hydroxyapatite and related calcium phosphate minerals, which comprise about one-half of the volume of intact dentin. This surface-demineralized layer is then impregnated with monomer solutions to fill and interact with the resulting collagen-rich surface layer. The monomers polymerize to form what has become known as a "hybrid layer" comprising interpenetrating synthetic restorative polymers and natural collagen polymers.

To date the process has been one of trial and error with specific primer compounds that have a very limited number of configurational groups that can interact with the highly diverse sites within the dentin substrate. By contrast the inventive product libraries of multifunctional and multi configurational molecules, the PCDs of the present invention, can interact better by having not only more ligand groups per molecule but also by having a vast variety of conformations of those ligand groups on different molecules of the "product library" used, which molecules, by automatic selection, will find and be "recognized" by docking sites. The PCDs can anchor with multiple interactions to collagen fibrils and denatured polypeptide portions of the collagen fibrils remaining exposed upon the removal of the previously reinforcing calcium phosphate crystallites.

Although in most contemporary chemical literature it is assumed that the readers know the definitions and limits of the terms "combinatorial synthesis," "combinatorial libraries," and others that are not unrelated to the present specification, it may be well to define and differentiate such as are used herein. "Combinatorial synthesis" herein comprises combining and reacting a specified amount of one or more cyclodextrin compounds with a specified amount of one or more reagent compounds in such a way as to produce a mixture of reaction products having substituents located in quasi-random configurations, having various combinations and permutations, on one or both of the two rims of the cone-shaped rings of the various cyclodextrin molecules. The term "quasi-random" is used because "random" would imply that all of the potential reaction sites were equally reactive, which in the case of cyclodextrins, they are not. The terms "combinatorial libraries," "product libraries," "PCD libraries," or "libraries" as used herein refers to the mixture of reaction products resulting from the combinatorial synthesis just described, either before or after purification procedures.

In contrast to conventional combinatorial organic synthetic procedures, which iteratively use combinatorial syntheses to produce combinatorial libraries together with assays or screening methods to select the one best compound for a particular purpose from the millions that have been synthesized, the procedures in the present invention retain most if not substantially all of the many heterogeneous monomeric molecules in the mixture of reaction products resulting from the combinatorial synthesis. This allows for the large variety of these monomeric PCD configurations to interact with the large variety of potential docking or anchoring sites that exist in complex substrates, such as, for example, partially decalcified dentin, enamel, bone, and many industrial and other materials.

Three-dimensional computer modeling of typical portions of type I collagen the type found in dentin, and a number of typical members of the anticipated cyclodextrin derivatives, the "PCD libraries" of this invention have indicated that multiple bonding interactions can occur between each of the modeled cyclodextrin derivative molecules and the modeled collagen. For example, the PCD's pendant carboxyl groups interacted with amino acid side chains such as lysine and arginine, together with hydrogen bonding and "hydrophobic bonding" along the collagen triple helix. Furthermore, some of the ends of teleopeptide groups attached to the triple-helical portion of the collagen molecule and single-chain peptides resulting from ruptured or denatured collagen in the models could fit within the hollow central core of cyclodextrin derivatives of the present invention. Thus, the PCDs may encircle ends of single peptide chains. According to the models, it was surprising to find that PCD compounds of this invention could also encircle and form "hydrophobic bonds" with the relatively hydrophobic side groups, such as phenylalanine, tyrosine, proline and others, of collagen. In the past, the importance of hydrophobic bonding, in an aqueous environment, in the configuring and structural integrity of proteins and of its role in the rates of intra- and intermolecular adaptations has been highly underrated.

It is also conceived that these multifunctional monomers, as they penetrate into the surface, can and will form crosslinking bridges with calcium ions by way of intermolecular carboxyl moieties on these polymerizable compounds. Binding to etched enamel should also be exceptionally good by a multiplicity of carboxyl groups interacting with calcium and multiple H-bonding with phosphate moieties of the highly mineralized enamel surfaces. Individual members within this multifarious collection of derivatives of cyclodextrin, "PCD library" can range from having one or two to substantially a maximum number polymerizable groups and a minimum number of polar ligand groups in the formulation of comonomers and, optionally, fugitive diluents. This number is not intended to be limiting and can be increased or decreased by altering the stoichiometries of the reagents used in the synthesis, depending on the proposed use and the best results determined empirically. Stoichiometries can be used that yield a distribution having sufficient polymerizable groups per molecule to provide organophilic characteristics and miscibility in comonomers for formulations used as binders for dental and other composites.

2. Description of the Prior Art

Although there are thousands of references to cyclodextrins and their derivatives in the general literature, e.g., Takeo et al., 1973; Colson et al., 1974; Bender and Komiyama, 1978; Saenger, 1984; Szejtli, 1984; Breslow, 1984; Poudrier, 1995, searches to date have revealed neither reports nor utilization of monomeric methacrylated cyclodextrin derivatives (MCDs) in dental resin formulations, combinatorial synthetic methods, or libraries, or assemblages of monomeric compounds that have multiple permutations of polymerizable and adhesion-promoting groups such as the polymerizable cyclodextrin derivatives (PCDs) conceived and taught herein. However, "MCDs" was used to designate methacrylated cyclodextrins when methacrylate groups were used as the polymerizable moieties in dental resin formulations (Bowen,1996). Early work by Bowen (1961) showed that certain surface-active comonomers could compete with water for attachment to hard tooth tissues.

An object of this invention comprises discovering many potentially useful dental applications of appropriately modified cyclodextrins. One application lies in composites, sealants, cements, and other resin formulations wherein polymerization shrinkage stresses might be reduced with perhaps less diminution of other desirable physical properties than by other means alone. As a mechanism, the relatively hydrophobic cavities within (meth)acrylated cyclodextrins house, prior to polymerization, appropriately sized comonomers that have relatively low dielectric constants, which, during polymerization, may become external network chain segments. The resulting empty, somewhat rigid cavities (~42 $Å^3$ per PCD molecule) comprise some of the free volume space otherwise lost during polymerization.

The need for monomers that polymerize and crosslink very rapidly, indifferent to the presence of water, with adequate water solubility and various surface-activity mechanisms including one based substantially on hydrophobic interactions, comprising partial molecular encapsulation of substrate moieties by components of the applied polymerizable resin adhesive resin, has not been adequately recognized.

Another problem associated with forming complex derivatives of CDS is an economical method of forming clearly homogeneous solutions so that probability statistics can be applied to form products of the desired characteristics. This requires solvated CD molecules that are not just suspensions of crystallites or of gelled aggregates when the reagents are added and mixed at rates lower than reaction rates.

The present conception includes the experimental use of sterically hindered tertiary alcohols (e.g., t-butyl alcohol) as well as mixtures of appropriate aprotic solvents and amines as solvents to obtain clear and homogeneous solutions of CDS for the syntheses of MCDs and PCDs. The rationale is based on the low $S_N2$ reactivity of tertiary alcohols compared with the primary and secondary alcohols of cyclodextrins. The feasibility of including hindered tertiary alcohols and the proportions of reagents to be used when including tertiary alcohols as components in obtaining clear solutions of CDS for combinatorial synthesis reactions to obtain useful PCDs must be determined empirically, and the mildest and most selective conditions and reagents feasible are recommended.

"Eutectic" mixtures can also be used to lower the melting point and increase the solubility of CDS in solvents and/or catalysts; in such cases the stoichiometries and relative reactivity rates must be taken into account. Eutectic mixtures of the high-melting, and relatively insoluble, CDS can utilize the relationship: $X=100(T_2-T_e)T_1+T_2-2T_e$, where X is the mole percentage of lower-melting component, $T_1$ is the melting point of the lower-melting component, $T_2$ is the melting point of the higher-melting component, and $T_e$ is the eutectic temperature which is the first sign of melting of the mixture.

U.S. Pat. No. 4,906,488 describes cyclodextrins amongst many "mers" for delaying the release of "permeants" to outside hosts but does not teach the use of combinatorial chemistry based on probability statistics to prepare specific diverse but related assemblages or libraries of surface-active comonomers for formulations suitable for adhesive and structural compositions.

U.S. Pat. No. 5,258,414, describes the incorporation of cyclodextrin or a complex of cyclodextrin and blowing agent into a thermoplastic to improve certain properties but does not disclose formulations or means to formulate compositions of the present invention.

U.S. Pat. No. 5,268,286, describes a method of immobilizing biocatalysts to various polymers that are unrelated to those of the present invention. They include cyclodextrin glucocyltransferase among the biocatalysts that can be immobilized. Cyclodextrin glucocyltransferase only synthesizes cyclodextrins [per se] from starch.

U.S. Pat. No. 5,290,831 describes cyclodextrins as stabilizers for polymerization starters of compositions quite different from those described herein.

In a preliminary attempt to synthesize MCDs, $\beta$CD was dissolved in methyl sulfoxide, also known as DMSO, an aprotic solvent in which $\beta$CD is quite soluble. However, during the course of the procedure, it was learned that methacryloyl chloride and methacrylic anhydride react with DMSO (Technical Bulletin, 1966), and no product was isolated. This is not in accord with the assertions of Nussstein et al., U.S. Pat. No. 5,357,012; furthermore, they apparently did not utilize appropriate probability statistics, because an average of "two polymerizable groups per cyclodextrin unit" would not assure that each molecule would have even one such group, which would be necessary to obtain maximum structural integrity provided by the present invention. While their products might be adequate for the packing of chromatographic columns, they did not teach means to simultaneously provide the adhesion-promoting ligands and molecularly encapsulated polymerization initiators in monomers suitable for dental, biological, and other high-performance structural and adhesive compositions disclosed herein.

U.S. Pat. No. 5,362,496 describes the preparation of nicotine-beta-cyclodextrin complexes.

A restrained, multifunctional reagent described in U.S. Pat. No. 5,414,075, is restricted from reacting with either itself or with other molecules of the same reagent. In its utilization, the reagent requires the abstraction of hydrogen atoms by external activation requiring the use of highly energetic ultraviolet light, which would not be acceptable in dental, medical, and many industrial procedures.

U.S. Pat. No. 5,416,181, includes cyclodextrins in a list of water-soluble components to prevent coalescence of water-insoluble polymeric particles in film-forming compositions.

SUMMARY OF THE INVENTION

The novel combination of properties of certain polyfunctional monomers and their formulations provides for an unprecedented variety of potential uses in dental, medical and industrial applications where low polymerization shrinkage, adhesiveness, and other valuable properties are in need of improvement, especially where adhesive bonding to dentin is desired.

For adhesive bonding applications, the quintessential monomers have more than one carboxyl or other ligand group per monomeric molecule, more than one methacrylate, acrylate and/or other group that can be polymerized by a free-radical mechanism, and are controllably hydrophilic. The carboxyl groups in the monomers or other ingredients can be used in the form of protonated carboxyl groups, dissociated carboxylate groups, salts, amine complexes, esters, amides, and/or other derivatives. The high crosslink density of these polymers gives greater strength, durability, and dimensional stability. Well-cured polymers prepared from these crosslinking monomers have improved dimensional and adhesive characteristics during and after polymerization. This is because monomers and formulations described herein can be soluble or miscible in water and also capable of dissolving water in the monomeric formulations. The proportionalities of carboxyl groups and other components determine the desired hydrophilicities for the formulations. When the PCDs are applied in proper diluent formulations, the large variety of configurations will allow for individual members, which are discrete compounds of the PCD library of diverse configurations, to bind selectively to their more stable binding sites on the sterically and chemically diverse aspects of the substrate.

An important feature is the amorphous nature of the PCD monomers, which distinguishes them from monomers that form crystalline solids. The viscosities of the monomer formulations can be adjusted to optimum levels by the use of added comonomers of lower viscosity.

The present invention provides means by which a broad spectrum of surface-active, adhesive, crosslinking monomers, which polymerize by a free radical mechanism, can be produced by novel synthesis methods that are described herein. The inventive conception includes the use of probability statistics to obtain new and useful mixtures of organofunctional PCD monomers. The statistics are used to predetermine the molar proportions of the synthetic reagents to obtain the desired proportions of polymerizable, ligand, and hydrophilic groups on individual members of a very large population of similar but diverse PCD molecules.

Another object of the present invention is to disclose novel complexes of polymerization photo initiators, which are practically water-insoluble, that are molecularly encapsulated (cf. Breslow, 1984) within water-soluble surface-active monomers, which complexes can penetrate and infiltrate into aqueous substrate environments and adsorb by multiple-bond interactions onto diverse substrates, including proteins such as collagen, and then, while bound to the surface, be subject to photoinduced reactions that produce free radicals on these bound complexes, which radicals can then be added onto by double-bonded carbon vinyl groups, or other groups capable of addition and chain-forming polymerization, for growth outward from these surface initiation sites into the bulk of overlying monomers, which will then form crosslinked polymers intimately, multiply and densely bonded to the substrate surface(s).

It is most advantageous to have surface-bound sources of initiation that will allow mobile monomer molecules to approach, add on to, and polymerize away from a substrate surface. The currently available photo initiators do not have surface-binding groups and a polymerizable vinyl group together; therefore, they are not optimal in their capability of bringing about maximally dense populations of linkages between polymers and substrate surface attachment sites.

Another object of the present invention is to disclose novel complexes of polymerization initiators, for example, benzoyl peroxide or N,N-dimethyl-p-toluidine, which are practically water-insoluble, that are molecularly encapsulated within the inventive SACs and comonomers, which complexes can penetrate and infiltrate into aqueous substrate environments and adsorb on diverse substrate sites.

Another object of the present invention is to provide compositions that can reduce polymerization shrinkage and also improve adhesive bonding by complying with the following adhesive bonding factors: (1) members of the composition should have "chameleonic" solubility characteristics by being capable of rearranging intramolecular configurations, with polar groups that can be turned inward or outward relative to organophilic moieties, to allow solubility in both polar liquids like water and relatively nonpolar liquids, like acetone, water-insoluble comonomers, etc., to allow diffusion to "anchor" sites; (2) members should have mutual spacial arrangements of hydrophobic groups or areas that fit, in three dimensions, with complimentary hydrophobic groups or areas on the substrate, e.g., collagen fibrils; (3) members should have complimentary charges (e.g.,—$NH^+$ –$O_2C$—) relative, in three dimensions, to accessible regions in the substrate; (4) members should have two or more anionic, e.g., carboxyl, groups arranged appropriately to allow for bridging by $Ca^{++}$ and/or other divalent or multivalent cations between molecules and with the substrate; (5) members should have structures that allow for multiple H-bonding, after approximation by the other mechanisms, to anchor on "recognition" sites; and, (6) members should contain at least two polymerizable groups to allow for the formation of a "monomolecular (co)polymer."

The inventive methods and products described herein provide for a broad spectrum of surface-active, adhesive, crosslinking monomers and comonomers, which polymerize by a free radical mechanism, produced by synthesis methods that utilize catalysts for the syntheses, some of which catalysts may be retained in the synthesis reaction products to further serve, at a later time, to aid in the polymerization of these monomers to yield improved adhesion qualities and other desirable characteristics not hitherto available.

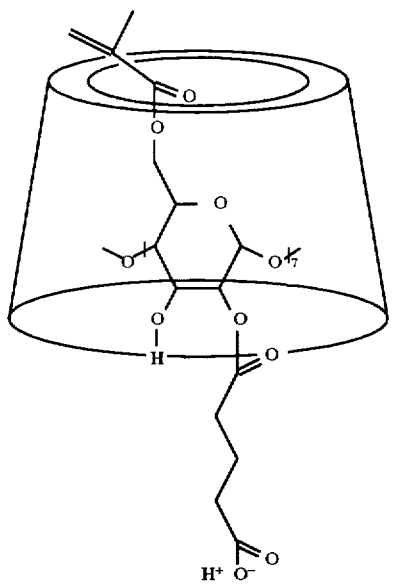

In the schematic shown here, only one example of a preferred configuration is depicted as a probable member of the millions of combinations and permutations that are formed during the combinatorial synthesis of novel structures in a βPCD product library. The polymerizable and ligand substituents and nonderivatized hydroxyl groups, 21 in all, are located in quasi-random configurations on the two rims of the cone-shaped ring of seven connected dextrose units. PCD molecules may also form inclusion complexes by encapsulating other molecules that can fit within the central spaces of the cones.

DESCRIPTION OF THE PREFERRED EMBODIMENTS

Of the potential uses of modified cyclodextrins in dental applications, uses also lie in adhesive bonding formulations. For example, dentin surfaces that have been superficially demineralized probably have disrupted collagen fibrils with regions of denaturation. Ruptures of the collagen molecules' triple-helical portions would probably present oligopeptide chains as end groups. Furthermore, at the ends of the triple-helical portions of intact type I collagen molecules, there are nonhelical teleopeptide chain extensions, which are relatively hydrophobic (Fietzek and Kühn, 1976). According to three-dimensional computer scale models, the inside diameters of βCD molecules can accommodate individual peptide chains. The outer dimensions are roughly the same as the diameters of collagen triple helixes. The ends of peptide chains and the larger, less-polar side groups of collagen's amino-acid segments e.g., phenylalanine, methionine, etc. might therefore allow for novel kinds of hydrophobic bonding contributions from appropriately designed PCDs.

For applications requiring high hydrophile/lipophil ratios (and/or adequate water solubility), such as adhesive bonding to dental and other hydrophilic surfaces, syntheses utilizing appropriate proportions of (meth)acrylic anhydride and/or cyclic anhydrides e.g., succinic, itaconic, maleic, phthalic, tetrabromophthalic, etc. per CD molecule can be used.

Hydrophilic PCD monomers and formulations described herein can be soluble or miscible in water to an extent between about 1% by weight and infinite miscibility and capable of dissolving at least about 1% by weight of water in the formulations or can be relatively insoluble in water as desired, by virtue of the fact that the proportions of hydrophilic and organophilic groups or components can be predetermined by the use of probability statistics together with the combinatorial synthetic methods disclosed herein.

It was discovered that if a large excess of methacrylic anhydride were used, practically all of the hydroxyl groups of the βCD molecule could be esterified by methacrylate groups, yielding products with very low water solubility. However, the use of increased proportions of cyclic anhydrides relative to methacrylic anhydride results in increased hydrophilicity. The addition reaction of cyclic anhydrides with hydroxyl groups of CD molecules results in monoester substituents that retain free carboxyl groups. These free carboxyl groups provide ligand functions with affinity for substrate sites and also allow for a wide range of miscibility with water, polar fugitive solvents, and hydrophilic monomers and formulations containing them. The activity of water in formulations can optionally be made approximately equal to that in biological tissues to promote biocompatibility and enhanced adhesive characteristics of polymers prepared from these formulations. One of the primary conceptions is that probability statistics can be used to determine in advance the proportions of hydrophilic ligand groups, e.g., carboxyl groups from the use of cyclic anhydrides, hydrophilic groups from unreacted hydroxyl groups, and organophylic groups, e.g., methacrylate or other polymerizable moieties to obtain PCDs most suitable for a given application. It was also conceived and is herein disclosed that catalysts, stabilizers, accelerators, chain-transfer agents, appropriate organophilic monomers, and polymerization initiators can be cornplexed hosted within the molecules of these PCD compounds so that they will not be separated by partitioning during penetration of the monomers into the substrate adherends, an essential feature of the invention.

The following illustrates how probability statistics can be used. A first problem was to determine how few moles of methacrylic anhydride or of other reagents, each molecule of which would attach a polymerizable monomeric group, M, per mole of βCD could be used and yet have at least one M group on each βCD product molecule. If in the reaction vessel there was a solution containing sufficient βCD (e.g., >$10^{10}$ molecules, or >~$10^{-13}$ mole) and if $N_c$ represented the number of βCD molecules, with the simplifying assumptions that each of the 21 hydroxyl groups (K=21) on the βCD molecules were equally reactive and that each M-producing reagent molecule would react with and only with βCD hydroxyl groups, then the question became one of determining the number ($N_m$) of M-producing reagent molecules to add in order to have at least a 95%) probability that at least 99% of the βCD molecules would acquire one or more attached polymerizable M group(s). If p denotes the very unlikely probability that a given βCD molecule would end up without any Ms, then $$p=(1-N_m/K\cdot N_c)^k$$

because $N_c$ and $N_m$ are so large. This relationship was based on combinatorial probability arguments that $$p = \frac{\binom{K\cdot N_c - K}{N_m}}{\binom{K\cdot N_c}{N_m}} \equiv \frac{\binom{K\cdot N_c - N_m}{K}}{\binom{K\cdot N_c}{K}}.$$

If X denotes the insignificant number of βCD molecules that end up without any Ms and X is to be less than 1% of $N_c$ and $N_m$ is large, it follows that the distribution of X is essentially Poisson, which distribution implies that its variance is equal to its mean. And because its mean is large (1% of $10^{10}$ is still very large), the Normal approximation to its distribution could be used. Thus to have Pr(X<0.01·$N_c$)= 0.95, it was necessary to have Pr((X−$N_c$·p )/($N_c$·p )$^{0.5}$< (0.01·$N_c$−$N_c$·p )/($N_c$·p)$^{0.5}$)=0.95 so that (from the Normal distribution) (0.01·$N_c$−$N_c$·p) /($N_c$·p)$^{0.5}$=1.645. The solution of the quadratic equation for p, in view of the size of $N_c$, gave $$p=0.01-0.1645/\sqrt{N_c}.$$

With the equating of these two expressions for p and solving for $N_m$.

$$N_m = K \cdot N_c (1-0.01^{1/k}(1-16.45/(K\sqrt{N_c})))$$

was obtained. Therefore in this case (where K=21 ), $N_m/N_c \geq 4.14$.

It should be noted, however, that the 21 hydroxyl groups on βCD molecules are not all equally reactive: Initially, the 7 primary hydroxyl groups of C(6) are the most reactive, the 7 secondary hydroxyls on the C(2) ring positions are somewhat less reactive, and least reactive are the 7 secondary hydroxyl groups on the C(3) positions. Steric hindrance also becomes a factor as reagents become attached to a given βCD molecule. These considerations greatly increase the probability that each product molecule would have at least one polymerizable group when the 4.1 4/βCD ratio is used and reacts so as to attach. Impurities and side reactions would obviously have the opposite effect. If reagents and reaction conditions are such that only 7 hydroxyl groups react, for example the primary hydroxyl groups of the C(6) positions, then $N_m/N_c \geq 3.38$. If 14 hydroxyl groups react, $N_m/N_c \geq 3.93$.

To obtain corresponding values for use with alpha-cyclodextrin, 6, 12, or 18 are used for K in the calculations described above. K=8, 16, or 24 are used for gamma-cyclodextrin derivatizations.

In order to be even more certain that crosslinking and multi functionality of ligand groups are possible with every product molecule, it would be desirable to have a minimum of at least two of each kind of groups on all molecules of the heterogeneous assembly of combinations and permutations to be used in the formulations for various applications. Accordingly, further statistical probability calculations were carried out to determine the molar ratio of reagent molecules to βCD molecules that should be used to ensure a high probability, >0.95, that at least 99% of each product molecule, in the libraries of PCDs, would have at least two such groups covalently bonded to it. The results of these calculations indicated that 5.8 moles of reagent per mole of βCD are needed in order to have a probability of 0.95 that at least 99% of the various PCDs' molecules will have more than one reagent group attached. For example, 5.8 moles of methacrylic anhydride per mole of βCD, each molecule of βCD having 21 reactive hydroxyl groups, if there is homogeneous mixing and random reactions with the hydroxyl groups, would yield a family of PCD molecules with an average of 5.8 methacrylate ester groups on the PCDs in general and more than one methacrylate ester group on each of the very small number of PCD molecules having the least number of methacrylate groups per molecule. Similar reasoning applies to other reagent compounds providing other types of polymerizable groups, ligand groups, or other functional groups.

On the other hand, to reserve for a special purpose at least one unreacted site (hydroxyl group on at least 99% of the βCD molecules with >0.95 probability), a proportion of 16.86 reagent molecules should be reacted per βCD molecule.

For use in applications wherein the symmetry and structural rigidity of the PCD scaffold rings are important, it may be desirable to limit the extent of derivatization of hydroxyl groups so as to conserve hydroxyl groups on the least-reactive C(3) atoms. By this means, intramolecular O(3)—H...O(2')hydrogen bonding can be retained so that the molecules'cores retain much of their potential inflexibility by analogy, relative to methylated cyclodextrins described by Harata (1991).

End use formulations may be prepared from the inventive PCDs described herein and adjusted to optimum viscosity levels by admixture with monomers of lower viscosity, water, and/or other miscible fugitive solvents. Comonomers include but are not limited to methacrylates, acrylates, dimethacrylates and diacrylates, oligomethacrylates and oligoacrylates, styrene, divinylbenzene, and others as may be appropriate for industrial and other uses or applications, with dimethacrylates being preferred.

It is important to utilize formulations with a potential for a high crosslink density and structural and dimensional stability of the resulting thermoset resin, because of the potential plasticizing effect of water and/or entrapped solvents. Water and/or miscible fugitive solvents might inadvertently be incorporated within the formulation during the polymerization, and/or imbibed, sorbed, or otherwise incorporated from surrounding environments before, during, and/or after polymerization occurs in situ. Fugitive solvents are defined herein as those that are volatile and intended to be fleeting and ephemeral, to assist in the application and penetration of the solutes.

POLYMERIZABLE GROUPS

To prepare the inventive PCDs, an appropriate average number or probability distribution of polymerizable groups are covalently attached. The reagents for this purpose may be of a homogeneous type or an admixture of different types of reagents, provided that they are adequately reactive with the hydroxyl groups of the CDS' scaffold and that the total number of these reagent molecules complies with the probability statistics described herein. These reagents include methacrylic and acrylic acid chlorides and anhydrides, maleic anhydride, itaconic anhydride, glycidyl methacrylate, glycidyl acrylate, 2-isocyanatoethylmethacrylate, 2-isocyanatoethylacrylate, 2-halo-ethylmethacrylate, 2-halo-ethylacrylate, 4-vinylbenzylchloride or bromide, and other reagents, known to those reasonably skilled in the art of chemistry, that can attach polymerizable groups to hydroxyl groups. The preferred reagents include methacrylic acid chloride, methacrylic anhydride, acrylic anhydride, and glycidyl methacrylate. The foregoing reagents can provide PCDs having substituents containing methacrylate, acrylate, vinyl, or other groups capable of free-radical polymerization.

It is also desirable to have at least one or more viscosity-controlling comonomer(s) in formulations comprising PCD compositions. These comonomers can be selected from one or more of the group comprising triethylene glycol dimethacrylate; 2-hydroxyethyl methacrylate; cyclohexyl methacrylate; benzyl methacrylate; methyl methacrylate; glycerol dimethacrylate; polyethylene glycol 400 dimethacrylate; polyethylene glycol 600 dimethacrylate; polyethylene glycol 400 diacrylate; PEG 1,000 dimethacrylate; polypropylene glycol dimethacrylate; triethylene glycol diacrylate; diethylene glycol diacrylate; diethylene glycol dimethacrylate; ethylene glycol diacrylate; ethylene glycol dimethacrylate; water-miscible, low-viscosity liquid dimethacrylates and diacrylates; divinyl reaction products of 4,8-bis(hydroxymethyl)tricyclo[5.2.1.0$^{2,6}$]decane with one or more members selected from the group consisting of methacrylic anhydride, methacryloyl chloride, acryloyl chloride, and acrylic anhydride; the divinyl condensation reaction products of 1,4-dimethylolcyclohexane with members selected from the group consisting of methacrylic anhydride, methacryloyl chloride, acryloyl chloride, and/or acrylic anhydride; styrene; divinylbenzene, and other compatible comonomers. Preferred comonomers include triethylene glycol dimethacrylate; 2-hydroxyethyl methacrylate; cyclohexyl methacrylate; benzyl methacrylate; methyl methacrylate, and glycerol dimethacrylate.

AMINES

Solvation of CDS, catalysis of esterification, etherification, and/or other reactions in the syntheses of PCDs, co-photoinitiation of polymerization, and acceleration of decomposition of certain peroxides (e.g., benzoyl peroxide) can be facilitated by one or more amines selected from the group consisting of ethyl-4-dimethylaminobenzoate, 1,8-diazabicyclo[5.4.0]undec-7-ene (DBU), pyridine, 4-(dimethylamino)pyridine, hexamethylenetetramine (methenamine), 1,4-diazabicyclo[2.2.2]octane (DABCO), quinuclidine, 2-quinuclidine carboxylic acid, N,N-dimethyl-p-toluidine, N,N-dimethyl-3,5-dimethylaniline, 4-tert-butyl-N,N-dimethylaniline, N,N-dimethylglycine, N-alkylated imidazoles, triphenylamine, other tertiary amines, triphenyl phosphine, and triphenyl antimony. N,N-dimethylaminoethyl methacrylate, N,N-diethylaminoethyl methacrylate, 4-vinylpyridine, 2-vinylpyridine, 1-vinylimidazole, N-vinylformamide, 1-vinyl-2-pyrrolidinone, and analogous compounds are amines that are monomers that can copolymerize with the new monomers of the present invention and also that would be useful for catalyzing the synthesis of the PCD monomers formed and associate with the carboxyl groups of the PCD monomers and may subsequently aid in the polymerization of the PCD formulations by photoinitiation in conjunction with camphorquinone and/or other cophotoinitiators. A tertiary amine that may simultaneously serve as a catalyst for the syntheses of the monomers, prevent premature polymerization, and later act synergistically with polymerization photo initiators is 2,6-Di-tert-butyl-4-(dimethylamino)methylphenol. Preferred amines include 1,8-diazabicyclo[5.4.0]undec-7-ene (DBU) and pyridine.

POROUS SOLIDS

Falling withing within the scope of this invention is the use, in the synthesis and/or purification of PCDs, of high-surface-area solids that may be organic or inorganic, synthetic or natural, acidic or basic, and ionic or relatively nonpolar. Such solids may be activated carbon, acidic or basic oxides or hydroxides, calcium phosphates, ionic-exchange resins, or mineral compositions comprising synthetic, natural, and/or altered natural minerals. Such minerals may include but not be limited to brucite, gibbsite, appropriate members of the kaolin-serpentine group that comprises kaolinite, dickite, nacrite, hydrated halloysite, chrysotile, antigorite, and lizardite, appropriate members of the pyrophyllite-talc group, appropriate members of the mica group that comprises muscovite and phlogopite, smectite, vermiculite, sepiolite, palygorskite, imogolite, allophane, illite, chlorite, montmorillonite, and other porous, expansible, or pillared minerals. Hydroxy polymers of aluminum, zinc, titanium, and pillared clays with minimal content of transition elements capable of redox reactions are preferred. Removal of residual pyridine, DBU, other amines, or other compounds used in the solvation of CDS or the synthesis of PCDs, as well as discoloring impurities, may be facilitated by binding to or ionic exchange with such resins or minerals.

CYCLIC MONOANHYDRIDES

To obtain acidic and acid-derived ligand groups on the PCDs, the CDS can be reacted with cyclic monoanhydrides, preferably in the presence of tertiary amines or other catalysts. Cyclic monoanhydrides that can be used include but are not limited to glutaric anhydride, succinic anhydride, maleic anhydride, phthalic anhydride, tetrabromophthalic anhydride, methyl succinic anhydride, itaconic anhydride, diacetyl-1 tartaric anhydride, 2-octen-1-ylsuccinic anhydride, hexahydro-4-methylphthalic anhydride, 1,2-cyclohexanedicarboxylic anhydride, 1,4,5,6,7,7-hexachloro-5-norbornene-2,3-dicarboxylic anhydride, 1-cyclopentene-1,2-dicarboxylic anhydride, 2,2-dimethylglutaric anhydride, 2,2-dimethylsuccinic anhydride, 2,3-dimethylmaleic anhydride, 2-dodecen-1-ylsuccinic anhydride, 3,3-dimethylglutaric anhydride, 3,3-tetramethyleneglutaric anhydride, 3,4,5,6-tetrahydrophthalic anhydride, 3,5-diacetyltetrahydropyran-2,4,6-trione, anhydride, 3-ethyl-3-methylglutaric anhydride, 3-methylglutaric anhydride, 3-oxabicyclo (3.1.0)hexane-2,4-dione, bromomaleic anhydride, cis-1,2,3,6-tetrahydrophthalic anhydride, cis-1,2-cyclohexanedicarboxylic anhydride, cis-5-norbornene-endo-2,3-dicarboxylic anhydride, cis-aconitic anhydride, citraconic anhydride, dichloromaleic anhydride, endo-bicyclo(2.2.2)oct-5-ene-2,3-dicarboxylic anhydride, exo-3,6-epoxy-1,2,3,6-tetrahydrophthalic anhydride, hexafluoro-glutaric anhydride, methyl-5-norbornene-2,3-dicarboxylic anhydride, methylsuccinic anhydride, octadecenylsuccinic anhydride, S-acetylmercaptosuccinic anhydride, tetrapropenylsuccinic anhydride, phenylsuccinic anhydride, 1,2,4-benzenetricarboxylic anhydride, 1,8-naphthalic anhydride, 2,3-diphenylmaleic anhydride, 2-phenylglutaric anhydride, 2-sulfobenzoic acid cyclic anhydride, 3,6-dichlorophthalic anhydride, 3,6-difluorophthalic anhydride, 3-hydroxyphthalic anhydride, 4,5-dichlorophthalic anhydride, 4-bromo-1,8-naphthalic anhydride, 4-methylphthalic anhydride, 5-chloroisatoic anhydride, diphenic anhydride, homophthalic anhydride, isatoic anhydride, N-methylisatoic anhydride, phenylmaleic anhydride, tetrachlorophthalic anhydride, tetrafluorophthalic anhydride, and other cyclic monoanhydrides and substituted aromatic and aliphatic cyclic monoanhydrides that do not inhibit polymerization or result in discolored or toxic products. Preferred cyclic monoanhydrides include glutaric anhydride, succinic anhydride, and maleic anhydride.

INITIATORS OF POLYMERIZATION

The present conception includes the utilization as complexes, within as well as external to the βCD and other PCD monomers of the aforementioned compounds, of free-radical polymerization initiators, so that they will migrate and penetrate aqueous and hydrophilic environments along with these monomers or otherwise be favorably affected in their rate or manner of inducing polymerization. The initiators may be organophilic and fit within the PCDs or have ionizable groups and/or have surface-active groups or moieties that render them cooperatively or independently substantive to substrates of interest to yield enhanced adhesive bonding characteristics to the formulations by virtue of initiation of polymer chain growth from molecules attached to the substrate. There are numerous free-radical polymerization initiators well known to those reasonably skilled in the art; a few of these include camphorquinone (2,3-bomanedione); camphorquinone-10-sulfonic acid (synthesis method described by Pande et al., 1980); and peroxides. AIBN (2,2'-azobisisobutyronitrile), its complexes or derivatives, and/or related compounds, and/or peroxides that initiate polymerization by heating, etc., may also be used. Preferred free-radical polymerization initiators include camphorquinone and peroxides such as benzoyl peroxide. These may be used alone or in co-photoinitiating amines, and/or accelerators for the decompositions of the peroxide(s), depending on the conditions of end uses.

POLYMERIZATION INHIBITORS AND STABILIZERS

One or more polymerization inhibitor or stabilizer must be used during the syntheses and storage of the monomers of the present invention: these must be of a nature that their effectiveness will not be lost by interaction with the reagents. Such inhibitors and stabilizers include but are not limited to the following: BHT, butylated hydroxy toluene; oxygen; 3,5-di-tert-butyl-4-hydroxyanisole (2,6-di-tert-butyl-4-methoxyphenol); 2,6-di-tert-butyl-4-(dimethylamino)methylphenol; and 2,5-di-tert-butyl hydroquinone, all of which have sterically hindered phenolic groups that are not subject to reaction with glycidyl or anhydride groups. Stabilizers are used in very small concentrations, typically 0.001 to 1% by weight of the overall monomer formulation. The preferred inhibitor and stabilizer is BHT, butylated hydroxy toluene used in a concentration of about 0.1%.

FORMULATION 1

In this formulation, PCDs containing polymerizable groups and also tertiary amino groups are produced for uses such as primers or adhesives to metal surfaces and/or other applications wherein amino ligand functionalities are desired. In the case of βCD substantially all of the 21 reactive hydroxyl groups can be reacted first with reagents comprising those which attach polymerizable groups, for example, methacrylic anhydride, methacryloyl chloride, acrylic anhydride, acryloyl chloride, glycidyl methacrylate, glycidyl acrylate, and/or other reagents providing electron-poor double bonds; then, per mol of purified product, a sum of between 5.8 and 15.2 (preferably about 10) moles of one or more secondary amines selected from the group comprising imidazole, N-phenylglycine, ring-substituted N-phenylglycine, ring-substituted N-phenylalanine, and other secondary amines, is reacted by adding to some of the double bonds by means of Michael addition reactions. By such a process a composition can be obtained wherein each molecule of these cyclodextrin derivatives contains to a high probability no fewer than two remaining free polymerizable groups per molecule and also contains to a high probability no fewer than one tert-amine substituent per molecule. Preferred secondary amines are selected from one or more of the group consisting of imidazole, N-phenylglycine, substituted N-phenylglycines, N-phenylalanine, ring substituted N-phenylalines, N-methyl-p-toluidine, and other secondary amines.

FORMULATION 2

Formulations are prepared containing PCDs that have not only polymerizable groups but also amino groups, for example, products of Formulation 1, wherein some or all of the amino groups have been converted into complexes with boron trifluoride ($BF_3$). By means such as this, one or more fluoride-releasing compound(s) is/are incorporated, and the monomers and/or their polymers might provide a slow release of fluoride ions as desired, for example, in dental-restorative or caries-preventive materials.

FORMULATION 3

Acidic cyclodextrin derivatives with or without polymerizable groups can also be prepared by use of cyclic anhydrides as reagents. For example, to βCD, partially dissolved in diethylmethylamine, can be reacted maleic anhydride or cyclic glutaric anhydride, at least 21 mol per mol of βCD, until dissolution and reactions are complete. Likewise one or more of the cyclic monoanhydrides listed above can be used as judged appropriate by one skilled in the art. Volatile solvents and/or catalysts can be removed by extraction, heat, reduced pressure, and/or other well-known means, and the products may be used in the formulation of cements by admixture with polyvalent cation compositions.

FORMULATION 4

For heat-curing applications, AIBN [2,2'-azobisisobutyronitrile], its analogs, benzoyl peroxide, t-butyl peroxide, per esters, other peroxides and/or other compounds, complexes or derivatives that initiate polymerization by heating or other forms of thermal activation may also be used, either as internal molecular complexes or external molecular mixtures with the MCDs or product libraries of PCDs and/or their formulations.

FORMULATION 5

A clear and homogenous N,N-dimethylformamide solution of βCD is prepared. To increase solubility if necessary, the βCD may be optionally admixed with lesser or eutectic amounts of alpha-cyclodextrin, gamma-cyclodextrin, and hydroxyalkylated derivatives of these CDS, provided that the probability statistics are proportionally adjusted to obtain the desired numbers of substituent groups. The βCD solution containing esterification catalysts, etherification catalysts, or both if appropriate, and a stabilizer, such as BHT butylated hydroxy toluene, against premature polymerization, is rapidly stirred while a sum of at least about 4.14, or preferably 5.8, up to but not more than approximately 16.86 moles per mole of βCD of one or more reagents providing polymerizable groups, including but not limited to those listed hereinabove under the heading "POLYMERIZABLE GROUPS," is added slowly. The mixing rate, and diffusion to obtain a homogeneous solution, should exceed the reaction rate(s), and practically anhydrous conditions should be maintained throughout. After these reactions are essentially complete, about 4.14 to about 16.86 moles per mole of βCD of one or more reagents providing ligand groups, including but not limited to those listed hereinabove under the heading "CYCLIC MONOANHYDRIDES," are likewise added. After these reactions are essentially complete, the N,N-dimethylformamide, byproducts, and impurities are removed by extractions with volatile solvents. This can be accomplished with the use of a strong mechanical stirrer and the alternate addition of solvents in which the PCD is practically insoluble but in which the N,N-dimethylformamide is miscible, such as toluene, removal of the supernatant phase, dilution with a PCD solvent such as ethanol, reprecipitation with solvents such as cyclohexane, acetone, and/or ether, and removal of the supernatant phase. This cycle can be repeated as necessary to obtain the desired degree of purity. To the final ethanol solution can be added the appropriate comonomers, stabilizers, polymerization initiators, and other ingredients, some of which may become the complexed "guests" in "host" PCD molecules. The ethanol may be allowed to remain or may be removed by facilitated evaporation.

FORMULATION 6

This combinatorial synthesis is like that of FORMULATION 5 except that the reagents providing polymerizable groups and the reagents providing ligand groups are mixed together before adding to the CD solution, providing that these reagent groups are compatible and do not unfavorably interact before or after they are added to the CD solution; furthermore, if the reaction rates of these reagents are adequately similar in their reactions with the CD's or CDS' hydroxyl groups, the mixed reagents may be gradually added to, react with, and bring into solution, suspensions of CDS, provided that the proportions are such that to a high probability, >0.95, every molecule in the resulting heterogeneous mixture of molecules in the PCDs contains at least one polymerizable group.

FORMULATION 7

A very large number of novel PCD structures (a "library") is formed by a combinatorial synthesis in which some or all and at least one of the hydroxyl groups of substantially all of the CD molecules are etherified by reaction with glycidyl methacrylate and/or glycidyl acrylate and in which some or all of the hydroxyl groups thereby generated on the 2-hydroxy-3-methacryloxypropyl and/or 2-hydroxy-3-acryloxypropyl ether substituents and/or some or all of the unreacted CD hydroxyl groups are esterified by reaction with cyclic anhydride molecules in such a manner that substantially all of the PCD molecules have one or preferably more than one carboxyl group(s). Preferred catalysts for this synthesis comprise DBU, triphenylamine, triphenyl phosphine, and triphenyl antimony.

FORMULATION 8

To each mole of dried β-cyclodextrin, dissolved in sufficient N,N-dimethylformamide to form a clear solution, is added 0.001 to 1 mole, preferably 0.01 mole, of 1,8-diazabicyclo[5.4.0]undec-7-ene (DBU), and is added 0.001 to 1 mole, preferably 0.01 mole, of BHT (butylated hydroxytoluene), all with continued stirring at about ambient temperature, and is added slowly dropwise about 6 moles of methacrylic anhydride; when esterification is complete, as indicated by any one of a number of analytical methods known to those skilled in the art of analytical chemistry, about 6 moles of cyclic glutaric anhydride, dissolved in N,N-dimethylformamide or an inert volatile solvent, is added slowly dropwise; when esterification is complete, as indicated by any one of a number of analytical methods known to those skilled in the art of analytical chemistry, the reaction products (herein referred to as a "PCD library" of various molecular-product configurations due to differing combinations and permutations in the reaction sites on the β-cyclodextrin molecules) are precipitated by dropwise addition (while stirring is continued) of toluene, 4-vinyl toluene, and/or other inert, preferably volatile, relatively nonpolar solvent(s) in which N,N-dimethylformamide, 1,8-diazabicyclo[5.4.0]undec-7-ene (DBU), and methacrylic acid are soluble or miscible; the supernatant is removed by decantation or filtration if necessary, and then the precipitated PCD library is diluted to a fluid consistency by admixture with ethanol, methanol, 2-hydroxyethyl methacrylate, and/or other polar and/or protic solvents that are miscible with both the PCD library and also with solvents that will precipitate the PCD library, such as those solvents just described; then, while maintaining as necessary an adequate stabilizer concentration of about 0.001 to 1%, preferably about 0.01 to 0.1% by weight relative to the theoretical yield of PCD library product material, this just-described process of precipitation and decantation or filtration is repeated until the unwanted solvents, catalysts, and/or byproducts are removed from the desired PCD library, as determined by analytical methods known and available to those skilled in the art. The derived polymerizable cyclodextrin derivatives ("PCDs") are then optionally formulated as desired by adding diluent comonomers, polymerization initiators, and/or other appropriate agents at the appropriate time as indicated for the desired end-use application(s), and packaged in a kit or otherwise for distribution and use. Falling within the scope of this invention are substitutions of suboptimal solvents, catalysts, stabilizers and details of procedure by those skilled in the relevant arts.

ADDITIONAL EXAMPLES

Additional Example 1

Substantially all of the 21 hydroxyl groups of beta-cyclodextrin (βCD) can be esterified to yield monomeric methacrylated beta-cyclodextrins (MβCDs) that are amorphous and soluble or miscible in dental resins and volatile solvents used in dental applications. Methods for synthesis and purification are described in the following examples. A residue of combinations and permutations of PCDs, polymerizable cyclodextrin derivatives, containing both methacrylate ester groups and hydroxyl groups was presumably obtained from evaporative concentration of the combined aqueous phases obtained in the purification of the MβCDs described below.

Additional Example 2

A stoichiometric excess of methacrylic anhydride (MAnh) was reacted with dried βCD (F.Wt.~1135) in pyridine. βCD (73 g as received, courtesy of American Maize-Products Co., Hammond, Ind., lot E6019-720) was dried in a vacuum oven (about 30 kPa, 108° C., 1 d) to a constant weight of 64 g. From this about 15 g (0.0137 mol; 0.288 OH equivalent) of βCD was combined with 0.0212 g BHT (butylated hydroxytoluene), 68.9 g of anhydrous pyridine, and 79.4 g of "94%" methacrylic anhydride (0.484 mol). The mixture was magnetically stirred in a closed round-bottom flask that was maintained at temperatures ranging between 28° and 50° C. for five hours, after which the heat was turned off and stirring was continued in the closed system at about 22° C. Subsequently, five different aliquots of the practically clear, very light yellow solution were withdrawn, and various methods were evaluated for separating the desired product(s) from the solvent and by-products. The aliquots were numbered in the chronological order taken.

Additional Example 3

Aliquot 1 (20 mL) was let down into 250 mL of stirred, 0° C. distilled water. BHT (butylated hydroxytoluene; 0.0027 g) was added, and stirring was continued during which time a very viscous cohesive product separated. The clear aqueous phase was decanted off, and the resin phase was dissolved in 25 mL of methanol. BHT (0.0054 g) was added to the clear solution, which was then concentrated in a desiccator having a partial vacuum (about 30 kPa) and indicating Drierite (W. A. Hammond Drierite Co., Xenia, Ohio). This produced a very viscous clear liquid that was then heated in an open vessel in a vacuum oven at about 105° C. for 4.5 h, cooled in a vacuum desiccator, and then stored in a refrigerator at about 0° C. This aliquot resulted in about 4.73 grams of a clear, light yellow glassy solid.

Additional Example 4

Aliquot 2 (20 mL) was filtered overnight by gravity through a Whatman #2 paper, yielding a clear light yellow filtrate. The filtrate was concentrated in a vacuum oven at about 110° C. for 3 d, yielding 7 grams of clear dark amber, very viscous liquid. It was then dissolved in methanol (29 g). To this solution, distilled water was added dropwise with stirring. Each addition produced "snowflakes" that dissolved in about 10 s. When 10.9 g of water had been added, the precipitated sediment appeared cohesive, and the supernatant was decanted off. The residue was redissolved by the addition of methanol, and the product was reprecipitated by the addition of water with vigorous stirring; a milk-white emulsion was produced. This mixture was gravity filtered (Whatman #42), and the filter cake was dried in a vacuum desiccator. The dry white powdery MβCD recovered (some was lost by spilling) was $\geq 2.0$ g.

Additional Example 5

Aliquot 3 (40 mL) was gravity filtered into a distilled water bath containing ice cubes (prepared from distilled water) during which time the bath was agitated with an ultrasonic generator. After the product phase had settled, the aqueous phase was gravity filtered through a Whatman #2 paper, producing a clear filtrate. The water-insoluble resin phase was air dried, resulting in a slightly off-white solid (11.6 grams), which was dissolved in methanol (~132 g) and filtered. With vigorous stirring of the filtrate, water (85 g) was added slowly to precipitate the product, which was separated by filtration. The product, dried in a vacuum desiccator, yielded 7.9 of white MβCD.

Additional Example 6

Aliquot 4 (40 mL) was gravity filtered through a Whatman #2 (medium) filter paper into a flask. The clear light amber filtrate (38.8 grams) was concentrated for 24 h in a rotary evaporator at about 50° C. with vacuum from a mechanical pump. The clear, viscous, amber, concentrated liquid (18 g) was thinned with methanol (~31 g) and then rapidly stirred while water (249 g) was slowly added. The supernatant above the precipitated material had an apparent pH of about 4, suggesting that residual methacrylic acid was present in the solution. The product was separated by filtration, redissolved with methanol (~32 g), precipitated again by addition of water (256 g), and separated by filtration. After vacuum desiccation, 7.8 g of off-white powder was recovered.

Additional Example 7

Aliquot 5, which was the remainder (29.7 g,~22 mL), was gravity filtered through a Whatman #2 (medium) filter paper into stirred, 65° C. distilled water, from which the product separated as an amber resin phase of relatively low viscosity. After cooling overnight, the resin phase was separated by filtration, "dried" in air (yielding 7.8 g), redissolved in methanol (20 g), and stabilized with additional BHT (0.008 g). Distilled water (393 g) was added slowly with stirring, giving a milk-white suspension of colloidal particles. The nominal pH of the suspension was about 6. These particles were collected on a filter and dried in air to yield a solid powdery material (6 g). This was again dissolved in methanol (39 g), filtered, and precipitated by adding water (414 g) with stirring. Gravity filtering overnight and drying with light vacuum for 10 d yielded a free-flowing, almost white powder (4.9 g). Samples from this aliquot were used for most of the procedures described below. The total MβCD recovered from these 5 trial procedures (~27.3 g) corresponded to a yield of about 80% of theoretical. The theoretical formula weight of fully methacrylated beta-cyclodextrin is about 2565.

Elemental analysis of a sample from aliquot 5 indicated the following. Found: C 58.62, H6.37, O 34.88, N not detected (<0.5%, the sensitivity of the method used); the theoretical values were C 59.01, H 6.05, O 34.94%. The "missing" 0.13% could represent N from residual pyridine and/or experimental error. Agreement within ±0.40% for C, H, and O is compatible with a MβCD product having ~21 methacrylate groups per molecule.

The $^{13}$C, $^{1}$H, and 2-D (2-dimensional heteronuclear correlation of $^{13}$C and $^{1}$H) NMR spectra also suggest that substantially every one of the hydroxyl groups had been esterified in the "purified," twice-precipitated, but substantially amorphous, samples of MβCD. Although in appropriate shift positions, the peaks in both proton and carbon spectra were often not sharp singlets, which broadening could be attributed to a number of causes (Casu et al., 1968).

An estimate of the number of hydroxyl groups on the cyclodextrins that were esterified to form methacrylate ester groups was obtained by integrating the proton nuclear magnetic resonance ($^{1}$H NMR) peaks. Deuterated chloroform, benzene, or methylsulfoxide (DMSO) solutions of aliquots 2 and 5 provided an isolated peak corresponding to the methacrylate CH$_3$ groups; however, the two protons on the vinyl sp$^2$ carbons gave peaks down field and confounded with the peaks corresponding to the 49 protons located on the 7 dextrose (glucose) rings of the βCD moiety. Therefore, calculations were necessary to "subtract" the vinyl protons from the total protons represented by the overlapping down-field peaks. The number of methacrylate groups divided by the number of βCD moieties thereby indicated the average degree of esterification. About five integrations and calculations were made on each sample solution, and the values were averaged to accommodate individual differences in the integrations. The overall average of 30 such integrations gave an estimation number of 24 (s.d. 11), which was slightly above the theoretical 21 methacrylate groups per molecule.

Qualitative solubility tests.

A few granules of the βCD or MβCD were placed on a microscope slide, covered with a cover glass, and examined with a polarizing microscope while a drop of liquid was placed to flow under the cover glass. These liquids comprised solvents having a wide range of solubility parameters and a number of monomers that might be of interest in dental or industrial formulations. Subjective solubility ranged from "practically insoluble," wherein the particles showing Brownian motion did not disappear and the corners of larger ones remained sharp, to "very soluble," in which cases all particles promptly went into a homogenous solution. With this method, βCD appeared as birefringent crystals that were very slowly and only slightly soluble in water and that were practically insoluble in methanol and in ethylene glycol dimethyl ether. In contrast, the MβCD particles appeared to be mostly amorphous and were very rapidly soluble (miscible) in methanol, promptly soluble in hydroxyethyl methacrylate and in benzyl methacrylate, slowly soluble in triethyleneglycol dimethacrylate and in 1,3-glycerol dimethacrylate, very slowly soluble in undiluted BIS-GMA, and practically insoluble in water.

Photopolymerization of an MCD.

Some of the MβCD product from aliquot 5 (0.2365 g) was dissolved in methanol (0.9850 g). Camphorquinone (CQ) (0.0152 g) was dissolved in methanol (0.6141 g). These solutions were combined, giving approximately a 1:1 CQ to MβCD molar ratio, and allowed to stand for 5 d. The cap of the vial was removed to allow slow evaporation of solvent while the solution was being stirred magnetically. When the clear fluid solution became slightly viscous, a one-drop sample was placed on a microscope slide and immediately spread under a cover glass, forming a thin sandwiched film. The film was exposed to a dental curing light for 10 s and then checked for cover-glass immobilization with a hand instrument. This exposure to light for 10 s was repeated until the cover glass could not be moved. In five replications, one sample "hardened," i.e., the cover glass was immobilized, between 10 and 20 s, three between 20 and 30 s, and one between 30 and 40 s.

Thermal interactions of MβCD with benzoyl peroxide (BPO).

According to Fisher-Hirschfelder-Taylor and computer-generated scale models, each MβCD molecule can have a central hollow space into which a smaller molecule of appropriate size can fit. Camphorquinone, benzoyl peroxide, and N,N-dimethyl-para-toluidine have sizes such that each of these could be hosted within MβCD molecules. MβCD was combined and shaken vigorously with BPO in a small vial; the proportions were one molecule of BPO per molecule of MβCD. Sufficient methanol was added to the sample to slowly form a clear solution. The methanol was then allowed to evaporate from the opened vial, while it was rotated slowly at about a 45 degree angle, to promote the "complexation" of the guest BPO molecules within the host MβCD molecules. After the mixture had dried to a thin glassy film on the inside of the vial, the open vial was placed in a desiccator with partial vacuum for further drying. The solid residue was pulverized with a flat ended glass rod to form a fine white powder.

A control material was a physical mixture of the MβCD and BPO powders, in the same proportions, combined and shaken vigorously in an identical vial. After drying in the desiccator, it was further mixed by stirring and gently triturating with a glass rod.

Aliquots of these powders were then placed in a simultaneous Differential Thermal Analyzer (DTA)/Thermogravimetric Analyzer (TGA; Harrop model ST-736). Heating rates were 2° or 3° C./min to determine the time and temperature of BPO thermal decomposition and/or the exothermic opening of the double bonds of the MβCD methacrylate groups. DTA/TGA comparisons of these powers were made with each vs. the other and each vs. an alumina control powder, the weights being equal to about ±0.1 mg. When these powders were heated slowly in the DTA/TGA analyzer, the time and temperature of BPO thermal decomposition and/or the exothermic opening of the double bonds of the MβCD methacrylate groups were distinctly different. The exotherms of the mixed powders preceded those of the "complexed" combination. These results are in accord with an interpretation that in the methanol solution the BPO had been substantially complexed as guests within the host MβCD molecules and that this complexation had thermally stabilized these BPO molecules relative to the particles of crystalline BPO in the mechanical mixture of the two powders.

Additional Example 8

A combinatorial synthesis was carried out wherein methacrylic anhydride and cyclic glutaric anhydride were both reacted with a clear solution of dried βCD (F.Wt.~1135) in a mixture of pyridine, an aprotic solvent, and a nonaromatic amine catalyst. βCD (167.8 g as received, courtesy of American Maize-Products Co., Hammond, Indi., lot G 6020-42) was dried in a vacuum oven (about 30 kPa, 110° C., 5 d), cooled and stored in a closed vacuum desiccator containing indicating Drierite®, yielding 145.6 g. A solution of 0.0424 g BHT (butylated hydroxy toluene; 2,6-di-tert-butyl-4-methyl-phenol) in 144 g of~anhydrous pyridine was magnetically stirred in a closed round-bottom flask and heated to about 55° C. Then 30.0 g (0.0264 mol; 0.555 OH equivalent) of the dried βCD was added, resulting in an almost-clear, translucent suspension that promptly became opaque white and difficult to stir. The suspension was at least as viscous at 94° C. as it was at 23° C. The addition of 32.0 g of N-methyl-2-pyrrolidone (1-methylpyrrolidinone) did not give apparent solubility improvement over the same temperature range. However, it was surprisingly discovered that when 1,8-diazabicyclo[5.4.0]undec-7-ene (DBU) was added (34.0 g, which was probably more than necessary) at 80° C., the suspension immediately became a clear, very light yellow solution. As it cooled to about 63° C., 25.1 mL of methacrylic anhydride (26.0 g, 6 mol per mol of βCD) was added from a dropping funnel into the stirring solution, the temperature being maintained by a prompt exotherm and the dropping rate during the 17 min of addition. Two h later, at 57° C., 19.0 g of glutaric anhydride (6 mol per mol of βCD), dissolved in 30 g of chloroform, was added dropwise over a 20 min period with a similar exothermic response. The clear, dark-amber solution that formed appeared to remain the same while it stirred in the closed flask for a number of days at about 23° C. This mixture of PCDs was purified by adding toluene dropwise while the mixture was stirred, letting the two phases settle, decanting off the toluene phase, thinning to a fluid consistency by the addition of anhydrous ethanol, and then repeating this procedure. Numerous one-mL samples were withdrawn, and these aliquots were mixed, in small glass vials equipped with poly(tetrafluoroethylene)-lined screw-caps, with volatile solvents having a wide range of solubility parameters to determine solubility characteristics, which assisted in further purifications as described in "FORMULATION 5." For example, to one of the one-mL samples was added one mL of reagent-grade acetone; the mixture was agitated vigorously, let settle into two equilibrated phases, and then the upper acetone-rich phase was removed by decantation. The lower, product-rich phase was heated to about 105° C. in the open vial in a vacuum oven (about 30 Kpa or 21 in. Hg. gage) for about 3 h, by which time the product had formed a slightly off-white open-cell solid foam. It was mechanically comminuted to a powder the particles of which were, when viewed under a polarizing microscope, glassy solids that dissolved immediately when water was added.

The rationale for the proportions of reagents used in the synthesis of this particular product library was that on average it would contain sufficient carboxyl and residual hydroxyl groups to provide sufficient affinity with water to allow its components to diffuse through water to access substrate surface sites, would comprise a PCD library or composition of millions of different combinations and permutations or configurations, have at least two polymerizable groups, hydroxyl groups, and carboxyl groups on virtually every molecule, and have the desired "chamelionic" characteristics for versatility and miscibility in comonomers and fugitive solvents to mix homogeneously with appropriate formulations containing them.

It is essential that the disparate classes of compounds or compositions be taken together as a whole, for this constitutes a major aspect of the invention, transcending the novelty of individual chemical compositions of matter.

REFERENCED PUBLICATIONS

Bender M. L., Komiyama M (1978). Cyclodextrin chemistry. New York: Springer-Verlag, pp. 1–39.

Bowen R. L. (1961). Investigation of the Surfaces of Hard Tooth Tissues by a Surface Activity Test. In: Proceedings of the Workshop on Adhesive Restorative Dental Materials. Phillips R., Ryge G., editors. At Indiana University, September 28–29, Spencer, Indiana: Owen Litho Service, pp. 177–191.

Bowen R. L. (1996) Synthesis of β-Cyclodextrin Methacrylates for Potential Uses in Dental Resins. J. Dent. Res., Vol 75:347, Abstract No. 2640.

Breslow R. (1984). Enzyme models related to inclusion compounds. In: Inclusion compounds, volume 3. Atwood J. L., Davies J. E. D., MacNicol D. D., editors. New York: Academic Press, pp. 484–508.

Casu B., Reggiani M., Gallo G. G., Vigevani A. (1968). Conformation of O-methylated amylose and cyclodextrins. Tetrahedron, 24:803–821.

Colson P., Jennings H. J., Smith Ian-CP (1974). Composition, sequence, and conformation of polymers and oligomers of glucose as revealed by carbon-13 nuclear magnetic resonance. JACS 96:25/8081–8086.

Fietzek P. P., Kühn K. (1976). The primary structure of collagen. In: International review of connective tissue research, volume 7. Hall D. A., Jackson D. S., editors. New York: Academic Press, pp. 28, 29.

Harata K. (1991). Recent advances in the X-ray analysis of cyclodextrin complexes. In: Inclusion compounds, volume 5. Atwood J. L., Davies J. E. D., MacNicol D. D., editors, New York: Oxford University Press, p. 342.

Poudrier J. K., (1995). Corn meets nanotechnology and they're getting along "amaizeingly" well. Today's Chemist at Work, February, pp. 25–30.

Saenger W. (1984). Structural aspects of cyclodextrins and their inclusion complexes In: Inclusion compounds, volume 2. Atwood J. L., Davies J. E. D., MacNicol D. D., editors. New York: Academic Press, pp. 231–259.

Szejtli J. (1984). Industrial applications of cyclodextrins. In: Inclusion compounds, volume 3. Atwood J. L., Davies J. E. D., MacNicol D. D., editors. New York: Academic Press, pp. 331–351.

Takeo K., Hirose K., Kuge T. (1973). Carbon-13 nuclear magnetic resonance spectra of cyclodextrins and its peracetates. *Chemistry Letters*, published by the Chemical Society of Japan, pp.1233–1236.

Technical Bulletin (1966). Dimethyl sulfoxide. Crown Zellerbach Corporation, Chemical Products Division, Camas, Wash. 98607, p 10.

What is claimed is:

1. A composition of matter comprising a library that is a mixture of derivatives of cyclodextrins, selected from the group consisting of α-cyclodextrin, β-cyclodextrin, and β-cyclodextrin, in which substantially each molecule in the library mixture of derivatives contains, according to predicted probability statistics, at least one covalently attached polymerizable group and wherein said composition also contains at least one stabilizing polymerization inhibitor and at least one polymerization initiator.

2. A composition of matter comprising a library that is a mixture of derivatives of cyclodextrins selected from the group consisting of alpha-cyclodextrin, beta-cyclodextrin, and gamma-cyclodextrin in which substantially each molecule in the library mixture of derivatives contains, according to predicted probability statistics, at least one covalently attached polymerizable group and wherein substantially each molecule within this library of polymerizable cyclodextrin derivatives also contains at least one covalently attached monoester group derived by reaction with at least one cyclic monoanhydride selected from the group consisting of glutaric anhydride, succinic anhydride, maleic anhydride, phthalic anhydride, tetrabromophthalic anhydride, methyl succinic anhydride, itaconic anhydride, diacetyl-1 tartaric anhydride, 2-octen-1-ylsuccinic anhydride, hexahydro-4-methylphthalic anhydride, 1,2-cyclohexanedicarboxylic anhydride, 1,4,5,6,7,7-hexachloro-5-norbornene-2,3-dicarboxylic anhydride, 1-cyclopentene-1,2-dicarboxylic anhydride, 2,2-dimethylglutaric anhydride, 2,2-dimethylsuccinic anhydride, 2,3-dimethylmaleic anhydride, 2-dodecen-1-ylsuccinic anhydride, 3,3-dimethylglutaric anhydride, 3,3-tetramethyleneglutaric anhydride, 3,4,5,6-tetrahydrophthalic anhydride, 3,5-diacetyltetrahydropyran-2,4,6-trione, anhydride, 3-ethyl-3-methylglutaric anhydride, 3-methylglutaric anhydride, 3-oxabicyclo(3.1.0)hexane-2,4-dione, bromomaleic anhydride, cis-1,2,3,6-tetrahydrophthalic anhydride, cis-1,2-cycloheexanedicarboxylic anhydride, cis-5-norbornene-endo-2,3-dicarboxylic anhydride, cis-aconitic anhydride, citraconic anhydride, dichloromaleic anhydride, endo-bicyclo(2.2.2)oct-5-ene-2,3-dicarboxylic anhydride, exo-3,6-epoxy-1,2,3,6-tetrahydrophthalic anhydride, hexafluoroglutaric anhydride, methyl-5-norbornene-2,3-dicarboxylic anhydride, methylsuccinic anhydride, octadecenylsuccinic anhydride, S-acetylmercaptosuccinic anhydride, tetrapropenylsuccinic anhydride, phenylsuccinic anhydride, 1,2,4-benzenetricarboxylic anhydride, 1,8-naphthalic anhydride, 2,3-diphenylmaleic anhydride, 2-phenylglutaric anhydride, 2-sulfobenzoic acid cyclic anhydride, 3,6-dichlorophthalic anhydride, 3,6-difluorophthalic anhydride, 3-hydroxyphthalic anhydride, 4,5-dichlorophthalic anhydride, 4-bromo-1,8-naphthalic anhydride, 4-methylphthalic anhydride, 5-chloroisatoic anhydride, diphenic anhydride, homophthalic anhydride, isatoic anhydride, N-methylisatoic anhydride, phenylmaleic anhydride, tetrachlorophthalic anhydride, tetrafluorophthalic anhydride, and other substituted aromatic and aliphatic cyclic monoanhydrides, and other cyclic monoanhydrides, that do not inhibit polymerization or result in discolored or toxic products, to provide monoester substituents that retain pendant carboxyl groups selected from the group consisting of protonated carboxyl groups, dissociated carboxyl groups, salts, amine complexes, and other carboxyl group derivatives, and wherein the covalently attached polymerizable substituents and said monoesters resulting from reaction with one or more cyclic monoanhydrides on the various individual molecules within this library mixture are located with various quasi-random permutations and combinations on the various individual molecules of this library mixture, and wherein said library mixture contains at least one stabilizing polymerization inhibitor.

\* \* \* \* \*